US008915957B2

(12) United States Patent
Arney et al.

(10) Patent No.: US 8,915,957 B2
(45) Date of Patent: Dec. 23, 2014

(54) DRUG DELIVERY STENT

(75) Inventors: Susanne Arney, Highland Park, NJ (US); Timofei Nikita Kroupenkine, Warren, NJ (US); Donald Weiss, Cresskill, NJ (US)

(73) Assignee: Alcatel Lucent, Boulogne-Billancourt (FR)

( * ) Notice: Subject to any disclaimer, the term of this patent is extended or adjusted under 35 U.S.C. 154(b) by 1985 days.

(21) Appl. No.: 10/798,064

(22) Filed: Mar. 11, 2004

(65) Prior Publication Data

US 2005/0203613 A1    Sep. 15, 2005

(51) Int. Cl.
*A61F 2/82* (2013.01)
*A61F 2/92* (2013.01)
*A61L 31/14* (2006.01)

(52) U.S. Cl.
CPC ......... *A61L 31/14* (2013.01); *A61F 2250/0002* (2013.01); *A61F 2/92* (2013.01); *A61F 2250/0067* (2013.01); *A61F 2250/0056* (2013.01); *A61F 2250/0039* (2013.01); *A61F 2250/001* (2013.01); *A61F 2250/0035* (2013.01); *A61F 2250/0068* (2013.01)
USPC ...................................................... 623/1.42

(58) Field of Classification Search
CPC ........... A61M 2037/0023; A61L 31/16; A61L 2400/18; A61L 2400/12; A61F 2250/0035; A61F 2250/0067
USPC ............. 623/1.15, 1.34, 1.39, 1.4, 1.42, 1.44, 623/1.46, 1.48, 1.23, 1.36, 1.2; 606/191, 606/194, 198; 604/31, 65, 66
See application file for complete search history.

(56) References Cited

U.S. PATENT DOCUMENTS 4,718,907 A  *  1/1988  Karwoski et al. ............ 427/2.25
5,655,548 A      8/1997  Nelson et al. ................. 128/898

(Continued)

FOREIGN PATENT DOCUMENTS

EP    1191121    3/2003    ............. C23C 14/48
JP    12678010   10/1998

(Continued)

OTHER PUBLICATIONS

B. R. Donald et al., "Power Delivery . . .," *J. Microelectromech. Syst.*, vol. 12, No. 6, pp. 947-959 (Dec. 2003).

(Continued)

*Primary Examiner* — Brian Pellegrino
(74) *Attorney, Agent, or Firm* — Michael J. Urbano

(57) ABSTRACT

An implantable stent comprises a tubular member having an interior surface and an exterior surface, with a region of at least one of the surfaces being hydrophobic. The region is provided with an array of microstructures or nanostructures that covers first portions of the surface but leaves second portions exposed in the interstices of the array. These structures cause the region to have a dynamically controllable hydrophobicity. In one embodiment, a control device, which is affixed to the tubular member, varies the hydrophobicity of the region. In another embodiment, which is particularly applicable to the delivery of a medicinal substance to fluids in body vessels, the stent also includes such a medicinal substance that adheres to the exposed portions until the control device alters the hydrophobicity of the region and causes the substance to be released into a body fluid in contact with the stent. Various ways to load the stent are described. In yet another embodiment, the tubular member is provided with a mechanism that enables the shape of the stent (e.g., its diameter) in vivo to be controlled dynamically, again by means of external wireless communication. In one more embodiment, sensors are affixed to the tubular member to enable fluid parameters (e.g., pressure, flow rate) to be monitored remotely.

20 Claims, 5 Drawing Sheets

(56) References Cited

U.S. PATENT DOCUMENTS

| | | | |
|---|---|---|---|
| 5,681,274 A | 10/1997 | Perkins et al. | 604/8 |
| 5,716,410 A | 2/1998 | Wang et al. | 623/12 |
| 5,855,599 A | 1/1999 | Wan | 623/1 |
| 6,185,961 B1 | 2/2001 | Tonucci et al. | 65/60.4 |
| 6,527,919 B1 | 3/2003 | Roth | 204/192.15 |
| 2003/0040791 A1* | 2/2003 | Oktay | 623/1.17 |
| 2003/0083646 A1 | 5/2003 | Sirhan et al. | 604/891.1 |
| 2003/0159920 A1 | 8/2003 | Roth | 204/192.12 |
| 2004/0030379 A1 | 2/2004 | Hamm et al. | 623/1.15 |
| 2004/0115239 A1* | 6/2004 | Shastri et al. | 424/423 |
| 2005/0027350 A1* | 2/2005 | Momma et al. | 623/1.42 |

FOREIGN PATENT DOCUMENTS

| | | | |
|---|---|---|---|
| WO | 9829030 | 7/1998 | A61B 5/02 |
| WO | WO 9964580 | 12/1999 | C12N 15/00 |
| WO | 02064019 | 8/2002 | |
| WO | 03072287 | 9/2003 | B23H 11/00 |

OTHER PUBLICATIONS

T. Akiyama et al., "Scratch Drive . . . ," *J. Microelectromech. Syst.*, vol. 6, No. 1, pp. 10-17 (Mar. 1997).

T. Krupenkin et al., "From Rolling Ball . . . ," *Langmuir Letters*, pp. A-D, and "Supporting Information," pp. 1-6, both available on the American Chemical Society website (2004).

J. Kim et al., "Nanostructured Surfaces . . . ," *IEEE Conf. MEMS*, Las Vegas, NV (Jan. 2002).

JPO action ("Examiner's Letter;" 3 pages) dated Oct. 6, 2010 in the Japanese application corresponding to U.S. Appl. No. 10/798,064.

WO 99/64580 listed above is, to the best of Applicants' knowledge and belief, an English language equivalent of JP National Publication No. 2002-517300 (Reference 1) cited by the JPO.

* cited by examiner

DRUG DELIVERY STENT

BACKGROUND OF THE INVENTION

1. Field of the Invention

This invention relates to stents that are implantable into body vessels or body cavities, and, more particularly, to such stents that are capable of controllably delivering doses of medicinal substances (e.g., pharmacological agents or drugs).

2. Discussion of the Related Art

Although we discuss below the specific problems associated with medical stents implanted in blood vessels, much of the discussion is applicable to stents implanted in other fluid-carrying vessels of the body.

Coronary artery disease, which is characterized by plaque build up and consequent narrowing of the artery (stenosis), is commonly treated by inserting implantable medical stents into the diseased portion of the artery to prevent it from becoming blocked. The solution is imperfect. One problem is that scar tissue can grow around the stent and block the artery. To reduce the formation of scar tissue some stents are coated or impregnated with a drug, which is passively eluded to inhibit tissue growth.

This type of drug-eluding stent has several disadvantages. First, passively eluding stents do not adequately inhibit the formation of scar tissue and may even produce blood clotting events. Second, the drug delivery mechanism is inflexible; i.e., it is predetermined by the mechanical attributes of the stent and the chemistry of the drug and its binding agents. No provision is made for controlled delivery of multiple doses and/or multiple drugs. Third, while a drug-eluding stent is typically made of a stainless-steel-like material, its shelf life is determined partly by the integrity of its sterile packaging but primarily by the limited lifetime of the drug component. Expired product must be removed from inventory at considerable expense to the user. This problem is exacerbated by the need to inventory stents having a variety of physical sizes. Fourth, static medical stents do not evolve dynamically as the physiology of the vascular system changes over time, which is problematic because replacing a stent is usually difficult, if not impossible, without surgical intervention.

Thus, there is a need in the art for a stent that is capable of remotely controlled delivery of one or more medicinal substances to a body fluid.

There is also a need in the art for a stent that is capable of remotely controlled delivery of multiple doses of one or more medicinal substances to a body fluid.

There is also a need in the art for a stent whose size can be dynamically and remotely controlled in vivo.

BRIEF SUMMARY OF THE INVENTION

These and other needs are addressed in accordance with one aspect of our invention, a stent comprising a tubular member having an interior surface and an exterior surface, with a region of at least one of the surfaces being hydrophobic. The region is provided with an array of microstructures or nanostructures that covers first portions of the surface but leaves second portions exposed in the interstices of the array. These structures cause the region to have a dynamically controllable hydrophobicity. In one embodiment, a control device, which is affixed to the tubular member, varies the hydrophobicity of the region. In another embodiment, which is particularly applicable to the delivery of a medicinal substance (e.g., a chemically active agent such as pharmacological agent or drug) to fluids in body vessels, the stent also includes such a medicinal substance that adheres to the exposed portions until the control device alters the hydrophobicity of the region and causes the substance to be released into the body fluid in contact with the stent. In still another embodiment, the control device is actuated by wireless communication with a transmitter located external to the body.

In order to load the medicinal substance into the stent before it is implanted, the substance may simply be dissolved into a solvent with sufficiently low surface tension (e.g., an alcohol) so that when it is spread over the array, the liquid automatically penetrates the interstices. When the solvent evaporates, the substance is deposited onto and adheres to the exposed portions. Alternatively, the substance may be dissolved in a solvent with a higher surface tension, so that when the solvent is spread over the array, it remains suspended over the microstructures or nanostructures; that is, it does not penetrate the interstices until the hydrophobicity of the region is reduced by applying a suitable voltage between the liquid and a conductive substrate that supports the microstructures or nanostructures.

In yet another embodiment, the tubular member is provided with a mechanism that enables the shape of the stent (e.g., its diameter) in vivo to be controlled dynamically, again by means of external wireless communication. In one more embodiment, the sensors are affixed to the tubular member to enable fluid parameters (e.g., pressure, flow rate) to be monitored remotely.

In still one more embodiment of our invention, the array of microstructures or nanostructures is tiled into electrically isolated areas that can be selectively addressed. Electro-wetting is used ex vivo to cover the entire array with a liquid, and a particular tile is electrically actuated to cause the liquid to load into that tile. Different tiles may be loaded with different drugs, for example, or with different doses of the same (or different) drugs. On the other hand, once the tiled stent is loaded, and is then implanted, any loaded tile may be remotely actuated to cause it to release its drug into the body fluid at controllable times.

In accordance with another aspect of our invention, we fabricate an implantable stent by first forming an elongated stack that includes a substrate of a first material and a layer of a second material on the substrate. The two materials have different thermal expansion coefficients. We form on a region of the stack an array of microstructures or nanostructures that allows the hydrophobicity of the region to be dynamically controllable. We also form a control device affixed to the stack for controlling the hydrophobicity. Then we heat the stack. The heating parameters (e.g., time, temperature), as well as the thicknesses of the substrate and layer and their thermal expansion coefficients, are mutually adapted to cause the stack to roll into a tubular member. In one embodiment of our method, the stack is first implanted and then heated in vivo by an electric current to cause it to roll up and form a tubular member.

BRIEF DESCRIPTION OF THE SEVERAL VIEWS OF THE DRAWING

Our invention, together with its various features and advantages, can be readily understood from the following more detailed description taken in conjunction with the accompanying drawing, in which.

DETAILED DESCRIPTION OF THE INVENTION

General Electro-Wetting Structure

Figure 1:
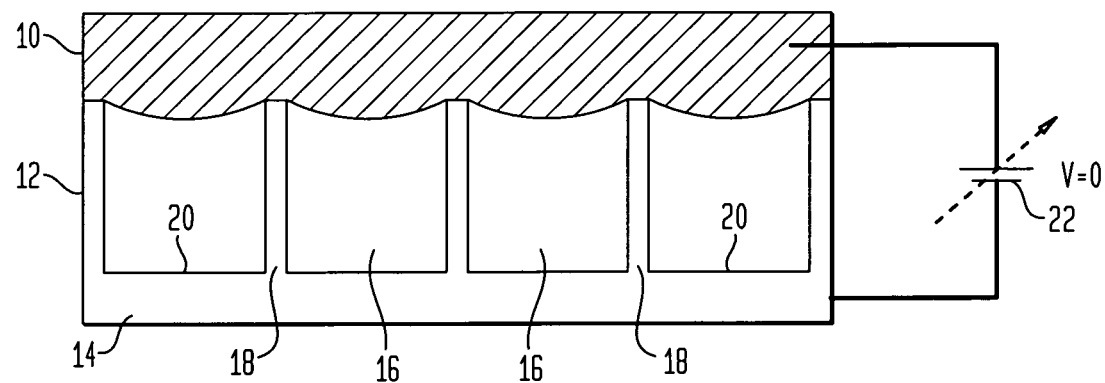
FIGS. 1-2 are a schematic, cross sectional views of the surface of a substrate that has been provided with an array of microstructures or nanostructures that allows the hydrophobicity of the substrate surface to be controlled by electro-wetting in accordance with the prior art.
Figure 2:
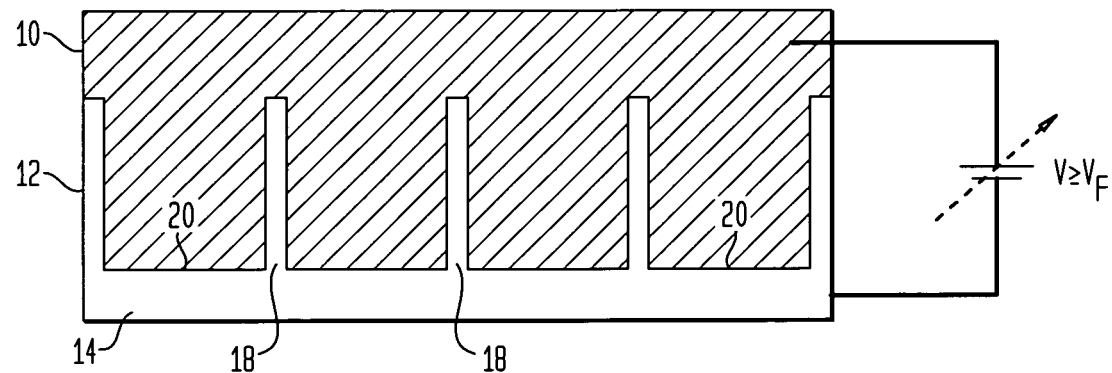

Before discussing our invention in detail, we first turn to FIGS. 1-2 in order to explain briefly how the hydrophobicity of a surface can be altered by means of an array of microstructures or nanostructures. As used herein, unless otherwise specified, a "nanostructure" is a predefined structure having at least one dimension of less than one micrometer, and a "microstructure" is a predefined structure having at least one dimension of less than one millimeter. Illustratively, the individual features of such structures have the shape of posts or pillars, which may themselves have the shape of cylinders or cones, for example. Illustratively, such features have a width in the range of about 4 µm to 20 nm, a height in the range of about 0.25 µm to 20 µm, and a spacing in the range of about 0.5 µm to 200 µm. The spacing of features in an array may be uniform or regular (e.g., periodic), or it may be nonuniform or irregular.

Nanostructured surfaces have been used to reduce the flow resistance of a droplet in microfluidic applications. See, for example, C. J. Kim, *IEEE Conf. MEMS*, Las Vegas, Nev., pp. 479-482 (2002), M. S. Hodes et al., copending U.S. patent application Ser. No. 10/674,448 filed on Sep. 30, 2003, and A. Kornblit et al., copending U.S. patent application Ser. No. 10/403,159 filed on Mar. 31, 2003, all of which are incorporated herein by reference. In addition, in a paper entitled "From Rolling Ball to Complete Wetting: The Dynamic Tuning of Liquids on Nanostructured Surfaces", T. N. Kroupenkin et al., *Langmuir* (February 2004; available on the website of the American Chemical Society) describe dynamic electrical control of the wetting behavior of liquids on nanostructured surfaces. This paper is also incorporated herein by reference.

In the discussion that follows we refer to the array of structures as nanostructures for simplicity only, with the understanding that in each case the term nanostructure includes the term microstructure, unless otherwise explicitly stated to the contrary.

In the prior art, an array of nanostructures 12 is formed on a conductive substrate 14, so as to cover first portions 18 of the substrate surface but to leave second portions 20 exposed by the interstices 16 between the structure features (e.g., between the posts of a nanopost array). A conductive liquid 10 is suspended over the array, and a variable voltage source 22 is coupled across the liquid and the substrate. To this end, the liquid and the substrate should be insulated from one another, typically by forming an electrically insulative coating (not shown) on the tops and sidewalls of the features and on the exposed portions 20 of the substrate 14. In addition, a low energy surface coating (not shown) is formed on the insulative coating in order to render the surface hydrophobic.

As described by Kroupenkine et al., Hodes et al. and Kornblit et al., supra, when no voltage is applied by source 22, as shown in FIG. 1, the hydrophobicity (surface tension) of the nanostructure array is sufficient to suspend the liquid 10 across the tops of the nanoposts; that is, the liquid does not penetrate the interstices of the array. On the other hand, the application of a low voltage (e.g., 10-20 volts) between the substrate 14 and the conducting liquid 10, decreases the contact angle that liquid 10 makes with each nanopost 12. As shown in FIG. 2, at or above a threshold or "fill" voltage, $V_F$, the liquid essentially fills the interstices and contacts the exposed portions 20. At this point we say that the liquid has penetrated the nanostructure array.

Drug Delivery Stent

In accordance with one aspect of our invention, the above principles of electro-wetting are exploited in an implantable stent in order to deliver one or more medicinal substances into a body fluid at controlled times and in controlled doses. Illustratively, the medicinal substance is a drug or other pharmacological agent; e.g., a substance that inhibits the growth of scar tissue or the clotting of blood in a coronary artery. Advantageously, the stent is loaded with the medicinal substance ex vivo at or around that time that the stent is needed; i.e., just prior to the time that the stent is to be implanted into a body vessel, which alleviates shelf-life problems. Of course, if shelf life is not an issue with respect to the particular medicinal substance, then loading may be done well in advance, and loaded stents may be inventoried for use as needed.

As is well known in medical arts, the stent is usually delivered to the body site by means of a catheter apparatus.

Figure 5:
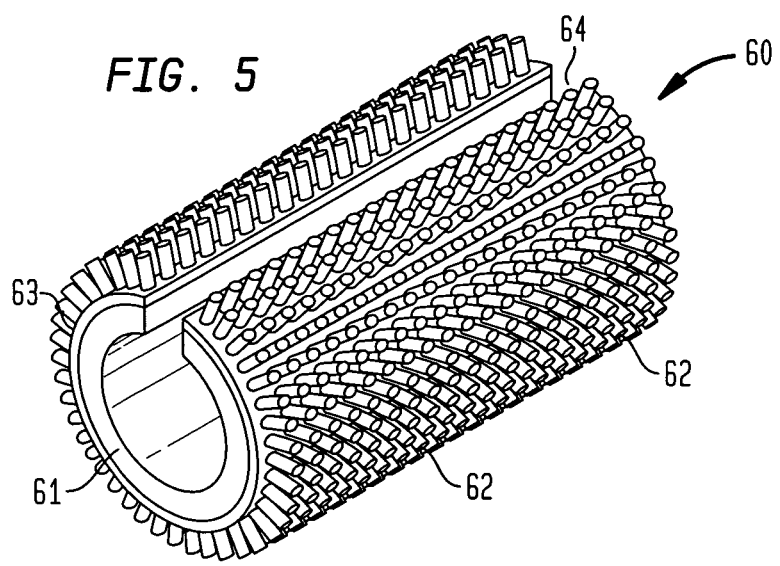

An illustrative embodiment of a stent 60 in accordance with this aspect of our invention is shown in FIG. 5. Stent 60 has the shape of a tubular member. The tubular member may be slotted cylinder having an elongated opening or slot 64, for example, or it may be a closed cylinder (not shown) depending on the processing technique used to fabricate the member. In addition, member 60 is shown as having an essentially circular cross-section, but in principle at least other cross-sectional shapes (e.g., elliptical, rectangular) may be suitable. One form of the slotted cylinder design, which will be described infra, is used to provide additional functionality; e.g., to adjust the shape of the stent.

Figure 3:
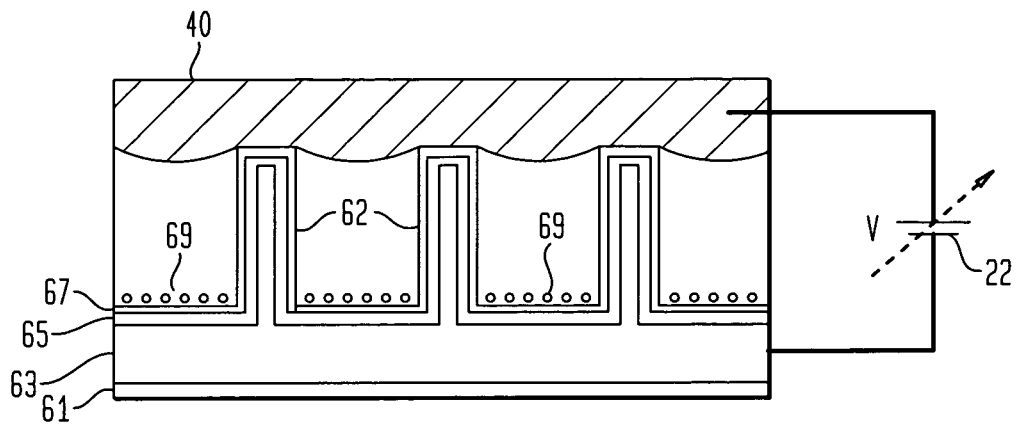
FIG. 3 is a schematic, cross sectional view of the surface of a stent that has been provided with an array of microstructures or nanostructures that allows the hydrophobicity of the stent surface to be controlled by electro-wetting and furthermore allows a medicinal substance adhering to the surface to be released into an overlying liquid, in accordance with one embodiment of our invention.

Turning now to FIG. 3, we show an illustrative design of the surface of a stent that has been provided with an array of nanostructures in accordance with one embodiment of our invention. Importantly, ex vivo a medicinal substance 69 has been disposed on and adhered to a portion of a hydrophobic layer 67 located at the bottom of the interstices of the nanostructure array 62. The nanostructure array 62, and hence the associated medicinal substance 69, may be located on the interior surface or the exterior surface of the stent, or both, depending on the desired therapeutic effect. For example, the nanostructure array 62 and its associated medicinal substance 69 would be advantageously placed on the outside surface of the stent, which abuts the interior wall of a coronary artery, in order to inhibit scar tissue growth. But, they would be advantageously placed on the interior surface, which abuts flowing blood, in order to more efficiently release drugs into the blood stream. For simplicity only, FIG. 5 illustrates the case where a nanostructure array 62 is disposed on the exterior surface of the tubular member.

The stent includes an electrically conductive outer layer or substrate 63 on which the nanostructure array 62 is disposed. Illustratively, the nanostructure array 62 comprises nanoposts, as shown. An electrically insulative layer 65 covers the upper surface of substrate 63 in order to electrically isolate the substrate 63 from the electrically conductive body fluid 40, and hydrophobic layer 67 covers the insulative layer 65. Layer 67 is hydrophobic in that it presents a low-energy surface (contact angle>90°) to any body fluid 40 that it contacts.

Illustratively, the substrate 63 comprises single crystal silicon, the insulative layer 65 comprises a silicon oxide, and the hydrophobic layer 67 comprises a polymer such as $CF_{1.5}$ or Teflon®. Typically, the nanoposts are about 300 nm in diameter, the silicon oxide is about 50 nm thick, and the $CF_{1.5}$ or Teflon layer is about 20 nm thick.

In operation, the stent is ex vivo loaded with medicinal substance 69. A simple technique for loading the stent is to dissolve the medicinal substance 69 in a low-surface-tension-solvent. When the substance-containing-solvent (SCS) is brought into contact with the nanostructure array 62, it automatically penetrates the interstices, evaporates, and leaves behind a residue of the medicinal substance 69 on the bottom of the interstices. (In practice, the residue of substance 69 would likely adhere also to the sidewalls of the array 62.) To make contact between the stent and the SCS the stent may be dipped into the SCS, or the SCS may be spread across the top surface of the nanostructure array. An alternative loading technique relies on electro-wetting and is describe infra.

Once loaded, the stent is delivered to the desired body site by means of a catheter. Body fluid 40 at the body site is suspended over the top of the nanostructure array 62, as depicted in FIG. 3, because the outer surface of the nanostructure has been rendered hydrophobic and initially no voltage is applied by source 22 between the substrate and fluid. However, once the stent has been implanted at the desired body site, the medicinal substance may be released into the body fluid by applying a voltage $V \geq V_F$, as described earlier in conjunction with FIGS. 1-2. This voltage causes the body fluid 40 to penetrate into the interstices and to contact the medicinal substance 69, which is then released into the fluid 40. The substance 69 diffuses into the fluid 40, where it may react with the fluid 40 or merely dissolve into it. The fluid 40 in turn brings the medicinal substance 69 (or the substance's reaction products, if any) into contact with body tissue, where it has a therapeutic effect (e.g., inhibiting the growth of scar tissue in coronary arteries, as discussed previously).

Figure 6:
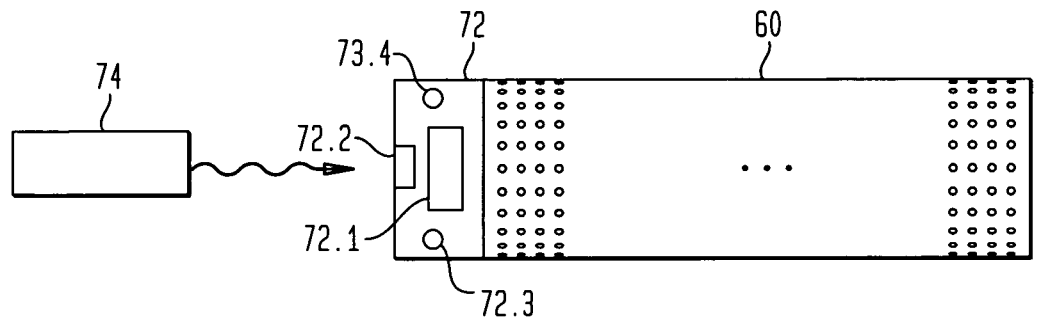
FIGS. 6-7 are schematic plan views of stents illustrating how a variety of devices are coupled to our stent, in accordance with yet another embodiment of our invention.
Figure 7:
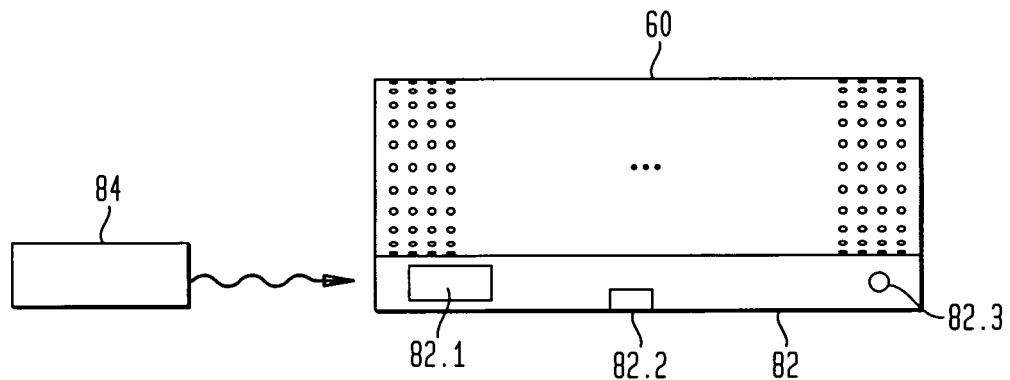

How the source 22 is actuated depends on when the medicinal substance 69 is to be released into the body fluid 40. Thus, if the substance 69 is to be released during the catheterization procedure, then the catheter apparatus may simply be provided with a wired connection between the in vivo source 22 and an ex vivo controller. Alternatively, a wireless connection may be utilized. The latter approach has certain advantages: first, it allows the medicinal substance 69 to be delivered at a later time for different therapeutic purposes without requiring further surgical intervention; and second, it allows additional functionality in that different substances 69 or different doses of one medicinal substance may be controllably delivered to the body at predetermined times, as described infra. Wireless communication with an implanted stent is illustrated in FIG. 6-7, in accordance with another embodiment of our invention. In FIG. 6 an electronic control wafer or chip 72 is affixed to one end of stent 60 and is oriented transverse to the elongated axis of the stent. Alternatively, chips could be affixed to both ends. In FIG. 7, on the other hand, an electronic control wafer or chip 82 is oriented parallel to the elongated axis of the stent. For example, if the stent is slotted, as shown in FIG. 5, the chip 82 could be affixed to one of the stent edges defined by the slot. Alternatively, chips could be affixed to both edges defined by the slot. In either case, the chip 72, 82 contains at least a receiver 72.1, 82.1 adapted to receive a wireless signal (e.g., an RF or optical signal) from ex vivo controller 74, 84. The receiver 72, 82 in turn provides signals that control the functionality of the stent; e.g., the application of voltage by source 22 and hence the delivery of a medicinal substance 69; or the alteration of the size of the stent as vessel physiology changes, as described infra in conjunction with FIGS. 10-12.

In addition, each chip 72, 82 may also include other devices or components, such as, for example, an electrical contact 72.2, 82.2, which makes contact with the body fluid, and/or sensors 72.3, 72.4, 82.3 that measure one or more body fluid parameters (e.g., pressure and/or flow rate). For differential sensing the embodiment of FIG. 6 is provided with a pair of sensors located at different positions along an axis transverse to the direction of fluid flow. In order for the results of such measurements to be communicated back to controller 74, 84, the chip 72, 82 could either be provided with a suitable transmitter, or chip 72.1, 82.1 could be designed as a transceiver.

Stents with Tiled Nanostructures

Figure 8:
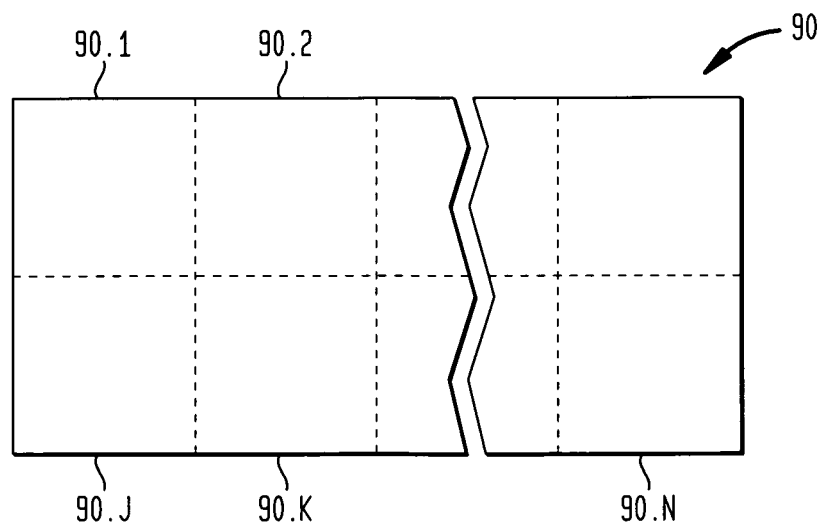
FIGS. 8-9 are schematic views of a stent in which the array of microstructures or nanostructures is tiled into electrically isolated zones and how electro-wetting is used ex vivo to load substances into selected zones or in vivo to release such substances from selected zones into body fluid, in accordance with still another embodiment of our invention.
Figure 9:
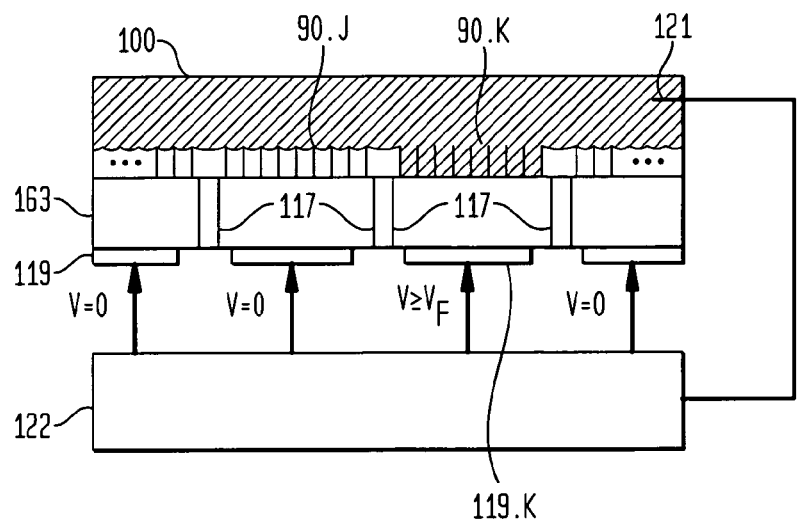

Turning now to FIGS. 8-9, we illustrate another embodiment of our invention, a tiled stent 90; that is, the nanostructure array of the stent 90 is segregated into a multiplicity of N>1 regions or tiles 90.1, 90.2, . . . 90.J, 90.K, . . . 90.N, which are electrically isolated from one another and separately controllable. More specifically, as shown in FIG. 9, each tile 90.J is formed on a region of substrate 163 that is surrounded by an electrically insulative wall or boundary 117. This isolation enables voltage source 122 to address tiles 90.1-90.N separately and independently; that is, the stent has a common contact 121 to the fluid 100, but separate contacts 119 to each of the tiles 90.1-90.N, so that voltage may be applied to each tile independent of the voltage, if any, applied to other ones of tiles 90.1-90.N.

In FIG. 9 we illustrate the case where only tile 90.K is addressed by applying a voltage $V \geq V_F$ between electrode 119.K and the fluid 100, which causes the fluid to penetrate the interstices of only tile 90.K. All of the other tiles are not addressed; hence V=0 is designated on the leads to each of the other electrodes 119. Obviously, in the general case a subset m (1≤m≤N) of tiles may be addressed simultaneously, if so desired.

This type of selective tile activation may be used either to deliver a medicinal substance from a particular tile 90.1-90.N (or subset of tiles) to a body fluid or to load a medicinal substance into a particular tile 90.1-90.N (or subset of tiles).

In the case of delivering a medicinal substance to a body, the fluid 100 is a body fluid and a multiplicity of tiles is loaded with either the same substance with the same or different doses; or different substances with the same or different doses. The tiled stent operates to dispense a medicinal substance from a particular tile 90.1-90.N into the fluid 100 only when that tile 90.1-90.N is addressed. Significantly, in this embodiment of our invention, the tile-controller may be programmed to address particular tiles 90.1-90.N at the same or at different times, thereby allowing the medicinal substances to be delivered to the body according to a predetermined therapeutic schedule.

Alternatively, in the case of loading a medicinal substance into a tiled stent, the stent operates to receive a medicinal substance into the interstices of a particular tile 90.1-90.N only when that tile 90.1-90.N is addressed. The fluid 100 might be a solvent in which a medicinal substance has been dissolved. The fluid 100 is spread over the surface of all of the tiles 90.1-90.N, but is loaded into only those tiles 90.1-90.N that are addressed; i.e., activated to be wettable by the fluid. The remaining fluid on the top of the tiles 90.1-90.N is then wiped or washed away or otherwise removed. Then, the solvent in a loaded tile 90.1-90.N evaporates, leaving behind a residue of the medical substance that adheres to the bottom (and/or sidewalls) of the interstices of the addressed tile 90.1-90.N. The process may then be repeated with a different medicinal substance or the same substance having a different dose, but these substances would be loaded into different (empty) tiles 90.1-90.N. Of course, if m=M, loading would not be selective; i.e., all tiles 90.1-90.N would be loaded with the same medicinal substance in the same dose. Once loaded and implanted, the various medicinal substances would be delivered into the body as described previously.

Stents with Controllable Size

Under certain circumstances the physiology of the body (e.g., of a blood vessel) changes, and it would be desirable to alter or adjust a physical parameter of an implanted stent. For example, it would desirable to be able to change the diameter of stent in vivo to accommodate corresponding changes in a coronary artery.

Figure 10:
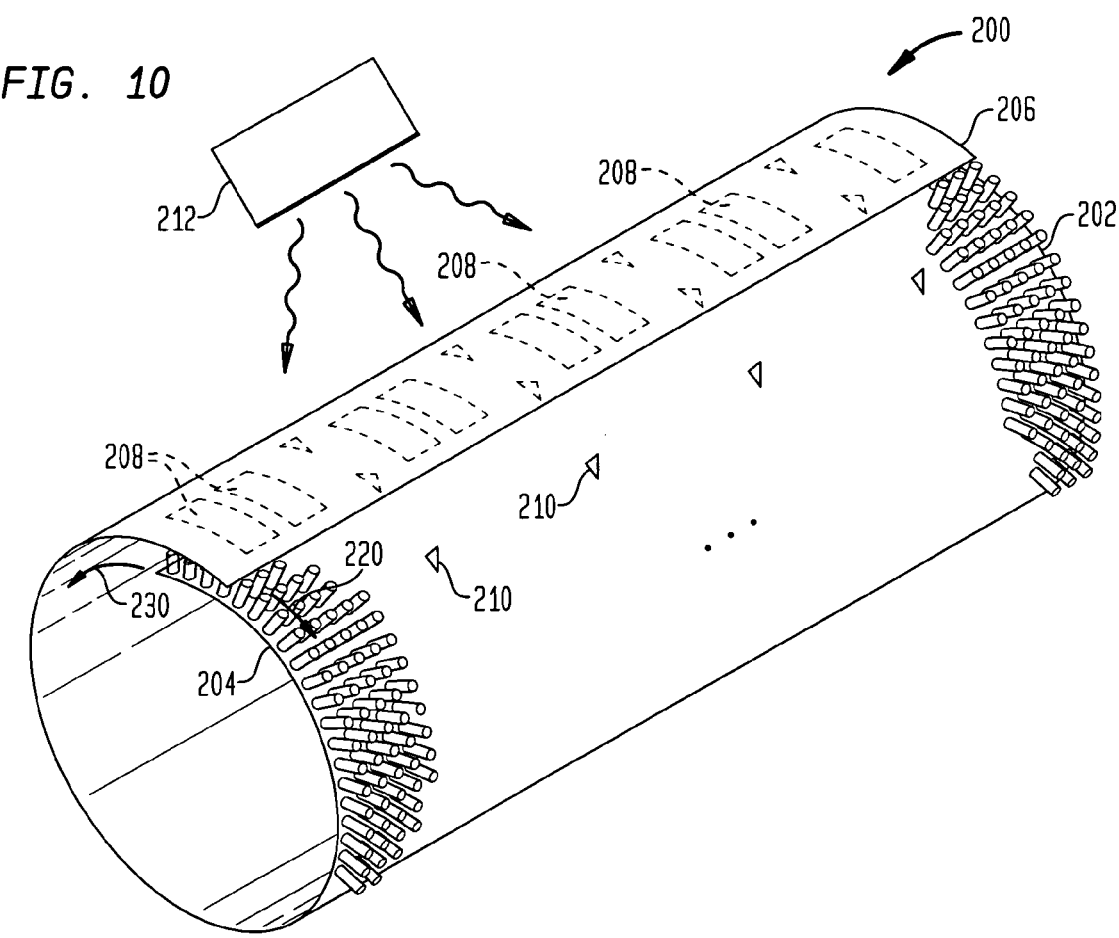
FIG. 10 is a schematic isometric view of one more embodiment of our invention in which a stent is provided with a mechanism for controlling its shape in vivo.
Figure 11:
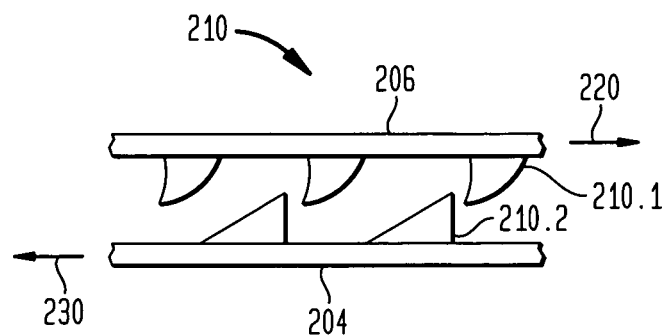
FIG. 11 is a schematic view of an illustrative ratchet and pawl used in the embodiment of FIG. 10.

FIGS. 10-12 illustrate an embodiment of a stent whose tubular member 200 is capable of making such adjustments in vivo by means of a remote controller 212. Although tubular member 200 is depicted as having a nanostructured surface 202, that feature is not essential to this aspect of our invention. In the stent, the tubular member 200 is formed by a surface that has been rolled upon itself so that end surfaces 204 and 206 overlap and are in close proximity to one another. In the overlapping region of the tubular member 200 we provide releasable latching mechanisms 210 and drive mechanisms 208. In response to a signal from remote controller 212, at least one of the drive mechanisms 208 is actuated to cause the end surfaces to advance in opposite directions, thereby either increasing or decreasing the diameter of the tubular member depending on which of the drive mechanisms are actuated. Once the desired movement has been completed, the latching mechanisms 210 releasably hold the end surfaces in place.

The drive mechanisms 208 may be actuated selectively so that the diameter of the tubular member 200 at one end is changed by an amount different from that at the other end. The number of drive mechanisms 208 that are utilized in any particular stent depends largely on the inertia or resistance of the tubular member to radial changes in it size.

As shown in FIG. 11, the releasable latching mechanisms 210 may be a simple ratchet and pawl arrangement in which the ratchet teeth 210.2, located on the lower end surface 206, engage the pawl teeth 210.1, located on the upper end surface 206, thereby preventing the end surfaces 204, 206 from slipping back after having been advanced by the drive mechanisms 208. The latching mechanisms 210 may be released by various means well known in the art including, for example, electrostatic or thermal means that cause surfaces 204, 206 to move farther apart, thereby disengaging the ratchet and pawl teeth from one another and allowing surfaces 204, 206 to slide relative to one another.

On the other hand, the drive mechanisms 208 may be well-known MEMS scratch drive actuators of the type described, for example, by T. Akiyama et al., *J. Microelectromech. Syst.*, Vol. 6, No. 1, pp. 10-17 (1997) or B. R. Donald et al., *J. Microelectromech. Syst.*, Vol. 12, No. 6, pp. 947-959 (2003), both of which are incorporated herein by reference. The principles of a scratch drive mechanism 208 are best understood by reference to FIG. 12, which shows that each mechanism 208 comprises a resilient, asymmetrically-shaped, conductive plate that includes first and second segments 208.1 and 208.2, respectively, oriented at an angle to one another. The asymmetry is realized by designing these segments to have different lengths; illustratively, segment 208.1 is longer than segment 208.2. In addition, the plate segments are anchored to the upper surface 206 of tubular member 200, illustratively at point 208.3, which may designate, for example, a joint or bend between the plates, but the segment tips 208.4, 208.5 are slidably disposed on, but electrically insulated from, lower surface 204.

Figure 12A:
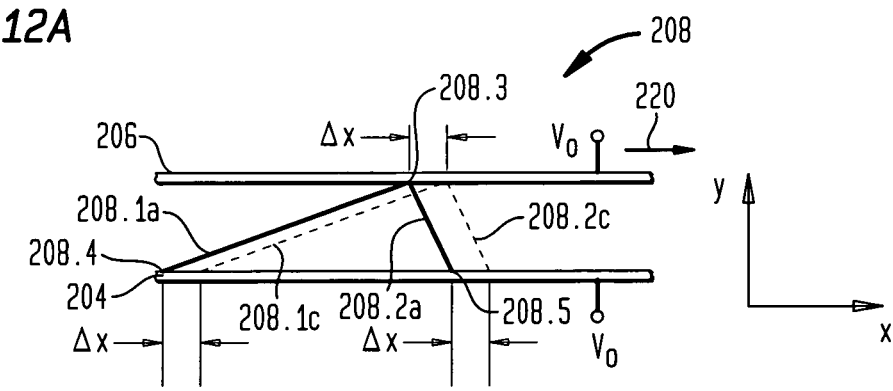
FIG. 12 is a schematic view of an illustrative scratch drive actuator used in the embodiment of FIG. 10.
Figure 12B:
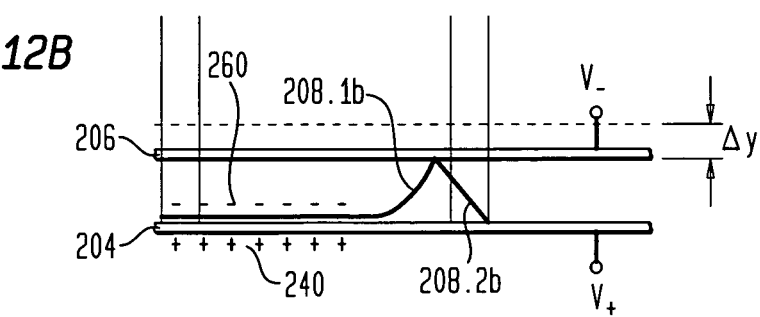

In operation, in a first quiescent state of the mechanism 208 the segments are designated 208.1$a$ and 208.2$a$, as shown in FIG. 12A. In this state the upper and lower surfaces 206 and 204, respectively, are held at the same electrical potential $V_o$. In a second actuated state a potential difference is applied across the upper and lower surfaces 206 and 204, respectively, by applying a voltage $V_-$ to the upper surface 206 and a voltage $V_+$ to lower surface 204. (To this end, these voltages are applied at points or regions of the surfaces that are electrically insulated from one another; e.g., by making the tubular member 200 of a multilayered SOI structure in which $V_-$ is applied to a Si layer and $V_+$ is applied to the Si substrate, which is electrically insulated from the Si layer.) As shown in FIG. 12B, the potential difference causes negative charge 260 to accumulate on segment 208.1$b$ and positive charge to accumulate on lower surface 204. The attraction between these oppositely poled charges causes segment 208.1$b$ to deform (e.g., to collapse downwardly), which in turn causes segment 208.2$b$ to slide or translate to the right (arrow 220) by a distance $\Delta x$ and temporarily causes the upper and lower surfaces 206 and 204, respectively, to move closer to one another by an amount $\Delta y$. Since the segments are anchored to the upper surface 206 at point 208.3, translation of the segments by an amount $\Delta x$ moves the upper surface 206 by the same amount. This movement is sufficient to increment the ratchet and pawl mechanism 210, which releasably holds the tubular member in its new position (representing a smaller diameter) after the voltage is removed. In its new, translated position, as shown in FIG. 12A, the segments 208.1$c$ and 208.2$c$ have returned to their original shape but have moved to the right by an amount $\Delta x$.

In a similar fashion, a subset of the scratch drive mechanisms 208 is modified to allow the diameter of the stent to be increased. For example, the modified mechanisms could simply have plates 208.1 and 208.2 interchanged with one another. Of course, this subset of mechanisms would be separately actuatable from the remainder of the mechanisms.

Self-Assembly Fabrication Process

A tubular stent of the type shown in FIGS. 5 and 10 is fabricated, in accordance with another aspect of our invention, by a self-assembly process that relies primarily on the difference in expansion coefficients of planar layers to cause them to roll up or coil into a tubular member when heated or cooled.

Figure 4:
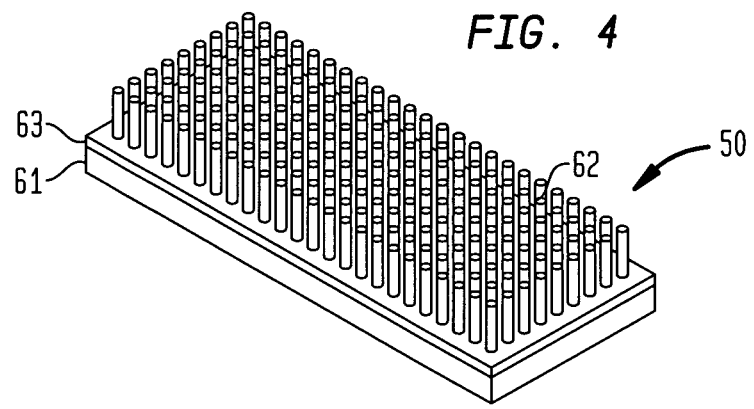
FIGS. 4-5 are schematic isometric views illustrating how a stent is fabricated in accordance with another embodiment of our invention.

More specifically, FIG. 4 shows a conductive first layer or substrate 63 in which a nanostructure array 62 is formed. Illustratively, the substrate 63 is made of conductive single crystal silicon. The nanostructure array 62 is formed in the top surface of the substrate by well-known photolithographic patterning and etching techniques, and then it is oxidized to form an electrically insulating layer (e.g., layer 65, FIG. 3). A second layer 61 is deposited on the bottom of substrate 63 to form stack 50. Next, a conformal polymer layer (e.g., layer 67, FIG. 3) is deposited on the oxide layer in order to form a hydrophobic surface.

The second layer 61 and substrate 63 are selected to have different thermal expansion coefficients. The various parameters (e.g., the thicknesses of the various layers, the thermal expansion coefficients of the layers, and the heating time and temperature) of the stack 50 are mutually adapted to cause the stack to roll up or coil into a tubular member in response to being heated or cooled, as shown in FIG. 5 or FIG. 10. For example, the stack 50 may be fabricated at an elevated temperature and then cooled to room temperature or to body temperature to cause the stack 50 to roll up.

From a materials standpoint, forming a nanostructure array in a semiconductor substrate 63 has the advantage that we can exploit the mature processing technology already developed by the integrated circuit industry. To this end, silicon is clearly preferred over other semiconductors at this time. However, one skilled in the art will readily recognize that, although not explicitly described above, other well-known methods of fabricating nanostructure arrays (e.g., embossing, stamping, printing, etc.) could be used in conjunction with other well-known materials (e.g., conductive plastics). On the other hand, the material of the second layer 61 merely has to have a sufficiently different thermal expansion coefficient from the substrate 63 to cause the stack 50 to roll up when heated or cooled. For the second layer 61, simple metals such as gold are suitable. However, more complex materials, such as well-known Ni—Ti-based "shaped memory" alloys (e.g., nitinol) may be preferred. These materials advantageously snap from a planar shape to a well-defined curved shape when heated above a threshold temperature.

It is to be understood that the above-described arrangements are merely illustrative of the many possible specific embodiments that can be devised to represent application of the principles of the invention. Numerous and varied other arrangements can be devised in accordance with these principles by those skilled in the art without departing from the spirit and scope of the invention. In particular, the self-assembly of our stent may take place in vivo. The planar stack 50 may be provided with electrical contacts (e.g., to the layer 61) coupled to a current source. After the stack is implanted, a control signal actuates the current source. Current flows through layer 61 and generates sufficient heat to cause the stack to roll up into the shape of a tubular member. As before, the control signal may delivered to the current source by a wired connection or a wireless one.

We claim:

1. An implantable stent comprising:
    a tubular member including an electrically conducting substrate and having an interior surface and an exterior surface,
    at least one of said surfaces being hydrophobic to a body fluid in that the contact angle between a droplet of said fluid and said at least one surface is greater than 90°, and
    a region of said at least one surface including an array of spaced-apart microstructures or nanostructures that covers first portions of said surface and leaves second portions exposed, said array causing said region to have a dynamically controllable hydrophobicity, said array forming interstices in the spaces between said microstructures or nanostructures,
    a chemically active substance adhered to at least one of said exposed second portions, said substance comprising a pharmacological agent or a drug,
    said electrically conductive substrate being configured to be electrically isolated from body fluid in contact with said array of microstructures or nanostructures,
    a control device affixed to said tubular member for varying said hydrophobicity, wherein said control device is capable of applying a voltage between said array and said substrate to vary the penetration of said interstices of said array by said fluid, thereby causing release of said agent or drug into said fluid,
    a hydrophobic layer covering said array within said region of said at least one surface, said layer being hydrophobic to said body fluid in that the contact angle between a droplet of said fluid and said at least one surface is greater than 90°, and
    said electrically conductive substrate and an electrically insulative layer disposed between substrate and said hydrophobic layer, said array being formed in said substrate.

2. The stent of claim 1, wherein said control device comprises an electronic device or an optical device.

3. The stent of claim 2, wherein said control device is remotely actuatable from an external source.

4. The stent of claim 1, wherein said array leaves second portions of said surface exposed, and further including
    means for electrically isolating said array into laterally separate spatial zones,
    at least two of said zones containing chemically active substances adhered to the exposed second portions thereof, and
    wherein said control device is capable of causing the release of said substances of the separate zones at different times.

5. The stent of claim 4, wherein said substances are the same chemically active substances of the same or a different dose.

6. The stent of claim 4, wherein said substances are different chemically active substances.

7. The stent of claim 1, further including means for altering the shape of said stent in vivo.

8. The stent of claim 7, wherein said altering means is capable of changing the diameter of said tubular member.

9. The stent of claim 1, wherein said tubular member has an elongated slot that is coextensive with its length, thereby forming a pair of elongated edges that are movable relative to one another, and the stent further comprising a plurality of electrically controllable structures thereon, the structures capable of moving said edges and releasably latching said edges.

10. The stent of claim 1, wherein said tubular member comprises a semiconductor substrate and said array of microstructures or nanostructures is disposed on said substrate.

11. The stent of claim 10, wherein said tubular member further comprises a layer disposed on said substrate, said substrate and said layer having different thermal expansion coefficients.

12. The stent of claim 11, wherein said microstructures or nanostructures have at least one dimension that is in the range of 4 μm to 20 nm.

13. An implantable stent comprising
    a tubular member including an electrically conductive substrate, said member having an interior surface and an exterior surface, at least one of said surfaces being hydrophobic to a body fluid in that the contact angle between a droplet of said fluid and said at least one surface is greater than 90°, and a region of said at least one surface including an array of microstructures or nanostructures formed by a multiplicity of spaced-apart pillars, the spaces between said pillars forming interstices, said array covering first portions of said surface, said array rendering the region to have a dynamically controllable hydrophobicity between a first state, in which said fluid is suspended over the top of said microstructures or nanostructures, and a second state, in which said fluid penetrates said interstices of said microstructures or nanostructures, a medicinal substance adhered to an exposed second portion of said surface located in said interstices of said microstructures or nanostructures, and a control device affixed to said tubular member for applying a voltage between said fluid and said substrate to vary said hydrophobicity, thereby releasing said substance into said body fluid when in said second state, said device being actuatable from an ex vivo source, a hydrophobic layer covering said array within said region of said at least one surface, said layer being hydrophobic to said body fluid in that the contact angle between a droplet of said fluid and said at least one surface is greater than 90°, and said electrically conductive substrate and an electrically insulative layer disposed between substrate and said hydrophobic layer, said array being formed in said substrate.

14. The stent of claim 13, wherein said exposed second portion includes laterally separate first and second spatial zones electrically isolated from one another, each zone containing a medicinal substance adhered thereto, and said control device is capable of causing the separate release of said substances from the first and second zones.

15. The stent of claim 14, wherein said substances adhered to said first and second zones are the same substance of the same or a different dose.

16. The stein of claim 14, wherein said substances adhered to said first and second zones are different substances.

17. The stent of claim 1 or 13, wherein said hydrophobic layer comprises a polymer.

18. The stent of claim 17, wherein said hydrophobic layer comprise a material selected from the group consisting of $CF_{1.5}$ and Teflon.

19. The stent of claim 1 or 13, wherein said substrate comprises single crystal silicon and said insulative layer comprises silicon oxide.

20. An implantable stent comprising a tubular member including a conducting substrate, an electrically insulative layer disposed on said substrate, and a hydrophobic layer disposed on said insulative layer, said hydrophobic layer being hydrophobic to a body fluid in that the contact angle between a droplet of said fluid and a surface of said layer is greater than 90°, a region of said substrate including an array of microstructures or nanostructures formed by a multiplicity of spaced-apart pillars, the spaces between said pillars forming interstices, said array rendering the region to have a dynamically controllable hydrophobicity between a first state, in which said body fluid is suspended over the top of said microstructures or nanostructures, and a second state, in which said fluid penetrates said interstices of said microstructures or nanostructures, a medicinal substance disposed within said interstices of said microstructures or nano structures, and a control device affixed to said tubular member for applying a voltage between said fluid and said substrate to vary said hydrophobicity, thereby releasing said substance into said body fluid when in said second state, said device being actuatable from an ex vivo source.

* * * * *